(12) United States Patent
Li et al.

(10) Patent No.: US 10,261,211 B2
(45) Date of Patent: Apr. 16, 2019

(54) NUCLEAR MAGNETIC RESONANCE LOGGING TOOL WITH QUADRATURE COIL CONFIGURATION

(71) Applicant: Halliburton Energy Services, Inc., Houston, TX (US)

(72) Inventors: Lilong Li, Humble, TX (US); Arcady Reiderman, Katy, TX (US)

(73) Assignee: Halliburton Energy Services, Inc., Houston, TX (US)

(*) Notice: Subject to any disclaimer, the term of this patent is extended or adjusted under 35 U.S.C. 154(b) by 210 days.

(21) Appl. No.: 15/509,478

(22) PCT Filed: Nov. 5, 2015

(86) PCT No.: PCT/US2015/059140
§ 371 (c)(1),
(2) Date: Mar. 7, 2017

(87) PCT Pub. No.: WO2017/078711
PCT Pub. Date: May 11, 2017

(65) Prior Publication Data
US 2017/0285216 A1    Oct. 5, 2017

(51) Int. Cl.
*G01V 3/32* (2006.01)
*G01V 3/18* (2006.01)
(Continued)

(52) U.S. Cl.
CPC .............. *G01V 3/32* (2013.01); *E21B 47/00* (2013.01); *G01N 24/081* (2013.01);
(Continued)

(58) Field of Classification Search
CPC ........ G01V 3/32; G01V 3/18; G01R 33/3678; G01R 33/4616; G01R 33/341; G01R 33/34053; G01N 24/081; E21B 47/00
(Continued)

(56) References Cited

U.S. PATENT DOCUMENTS 7,268,555 B1 * 9/2007 Rabinovich .............. G01V 3/28
324/338
2002/0153887 A1   10/2002 Taicher
(Continued)

OTHER PUBLICATIONS

International Search Report and Written Opinion for PCT/US2015/059140 dated Jul. 28, 2016.

*Primary Examiner* — Susan S Lee
(74) *Attorney, Agent, or Firm* — Gilliam IP PLLC

(57) ABSTRACT

Nuclear magnetic resonance (NMR) logging tools may be configured for situation-dependent NMR logging operations by including two dissimilar coils that may function in four different modes of operation based on logging conditions including: a resistivity of the fluid, a diameter of the wellbore, a depth into the subterranean formation of the volume of investigation, or a combination thereof. For example, an NMR logging tool with a z-coil and a transversal coil may be useful in generating in a volume of investigation of a subterranean formation either (1) a transversal radiofrequency (RF) excitation with the transversal coil or (2) a quadrature RF excitation with both the z-coil and the transversal coil, where the choice of transversal or quadrature RF excitation is based on the logging conditions; and detecting an NMR signal from the subterranean formation with one of: (1) the transversal coil or (2) both the z-coil and the transversal coil.

24 Claims, 2 Drawing Sheets

(51) Int. Cl.
*E21B 47/00* (2012.01)
*G01R 33/46* (2006.01)
*G01N 24/08* (2006.01)
*G01R 33/36* (2006.01)
*G01R 33/34* (2006.01)
*G01R 33/341* (2006.01)

(52) U.S. Cl.
CPC ..... *G01R 33/3678* (2013.01); *G01R 33/4616* (2013.01); *G01V 3/18* (2013.01); *G01R 33/341* (2013.01); *G01R 33/34053* (2013.01)

(58) Field of Classification Search
USPC .......................................................... 324/303
See application file for complete search history.

(56) References Cited

U.S. PATENT DOCUMENTS

| | | | |
|---|---|---|---|
| 2003/0090269 A1* | 5/2003 | Fanini | G01V 3/28 324/339 |
| 2004/0046552 A1 | 3/2004 | Taherian et al. | |
| 2008/0030415 A1* | 2/2008 | Homan | H01Q 1/04 343/719 |
| 2009/0072825 A1 | 3/2009 | Prammer et al. | |
| 2009/0292473 A1 | 11/2009 | Kruspe et al. | |
| 2010/0277176 A1* | 11/2010 | Homan | E21B 47/102 324/333 |
| 2011/0187372 A1 | 8/2011 | Kruspe | |
| 2011/0238312 A1* | 9/2011 | Seydoux | G01V 3/22 324/333 |
| 2012/0092015 A1* | 4/2012 | Dashevsky | G01V 3/24 324/324 |
| 2012/0109527 A1* | 5/2012 | Bespalov | E21B 7/04 324/339 |
| 2013/0043884 A1* | 2/2013 | Le | G01V 13/00 324/601 |
| 2013/0093422 A1* | 4/2013 | Morys | G01V 3/32 324/303 |

\* cited by examiner

NUCLEAR MAGNETIC RESONANCE LOGGING TOOL WITH QUADRATURE COIL CONFIGURATION

CROSS-REFERENCE TO RELATED APPLICATIONS

The present application claims the benefit of priority under 35 U.S.C. § 371 as a national stage application of PCT International Application Ser. No. PCT/US2015/059140 entitled "NUCLEAR MAGNETIC RESONANCE LOGGING TOOL WITH QUADRATURE COIL CONFIGURATION," filed on Nov. 5, 2015, which is hereby incorporated by reference in its entirety for all purposes.

BACKGROUND

The present application relates to an NMR logging tool and related methods.

Well logging is a common practice in the oil and gas industry to evaluate underground formations for the presence and producibility of subterranean formations. Among the most important parameters determined in the process are the depth and thickness of formation layers containing hydrocarbon, the formation porosity (i.e., the relative amount of void space in the formation), the hydrocarbon saturation (i.e., the relative percentage of hydrocarbons versus water in the pore space), and the permeability of the formation (i.e., the ability of the oil, gas, or water to flow out of the formation, into the well and eventually to the surface for recovery).

Presently, nuclear magnetic resonance (NMR) logging is considered one of the most effective techniques for determining these geologic parameters. NMR logging utilizes an NMR logging tool coupled to a drill string for analyzing the surrounding formation during a drilling operation.

NMR technology has many advantages over other logging techniques (such as gamma ray logging, sonic logging, electric logging, and others), one of the most significant being the independence of NMR measurements from formation lithology. In particular, NMR data relates in a simple manner to formation pore sizes. This relationship facilitates detection of formation fluids (e.g., gas, oil, and water) independent of the matrix mineralogy. To this end, in addition to estimation of formation porosity, hydrocarbon saturation, and permeability, NMR logging enables computation of clay-bound water, capillary-bound water, and free fluid volumes, which aid in comprehensively evaluating the subterranean formation.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present application relates to improving the signal-to-noise ratio (SNR) for an NMR logging tool with a quadrature coil configuration that uses two dissimilar coils.

NMR logging tools typically include only a single coil for analyzing the surrounding formation. However, the quality of the NMR measurements depend on, inter alia, the logging environment and the parameters of the NMR measurements. Accordingly, individual NMR logging tools are produced with specific single coil configurations to optimize or enhance the quality of the NMR measurements. However, if the conditions change (e.g., the composition of the fluid or the parameters of the NMR measurements change), the quality of the NMR measurements may significantly decrease. Such fluids may be drilling muds (also referred to herein as "mud").

The present application uses two dissimilar coils, which allows for four different modes of operation, when performing NMR measurements. The presently-described NMR logging tools are configured for situation-dependent NMR logging operations. That is, the mode of operation may be chosen before and/or during an NMR logging operation based on the logging environment and the parameters of the NMR measurements. To achieve the four different modes of operation, the NMR logging tools comprise two dissimilar coils.

The two dissimilar coils (e.g., a z-coil and a transversal coil) may have substantially different power consumption during pulsed excitation and different efficiency during reception depending on (1) the logging environment (e.g., fluid resistivity and wellbore diameter) and (2) the frequency band used in a multi-frequency logging tool (e.g., the depth of the volume of interested into the surrounding formation). Additionally, the two dissimilar coils may have different sensitivity with respect to the orientation of the signal when the NMR logging tool is designed for side-looking operation and, consequently, very different wellbore signal levels. The use of the two dissimilar coils, therefore, allows for situation-dependent NMR logging operations.

Figure 1:
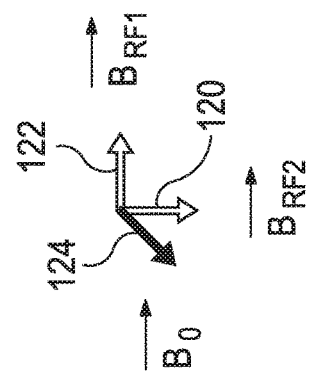
FIG. 1 illustrates an exemplary quadrature coil configuration suitable for use in a side-looking NMR logging tool.
Figure 1:
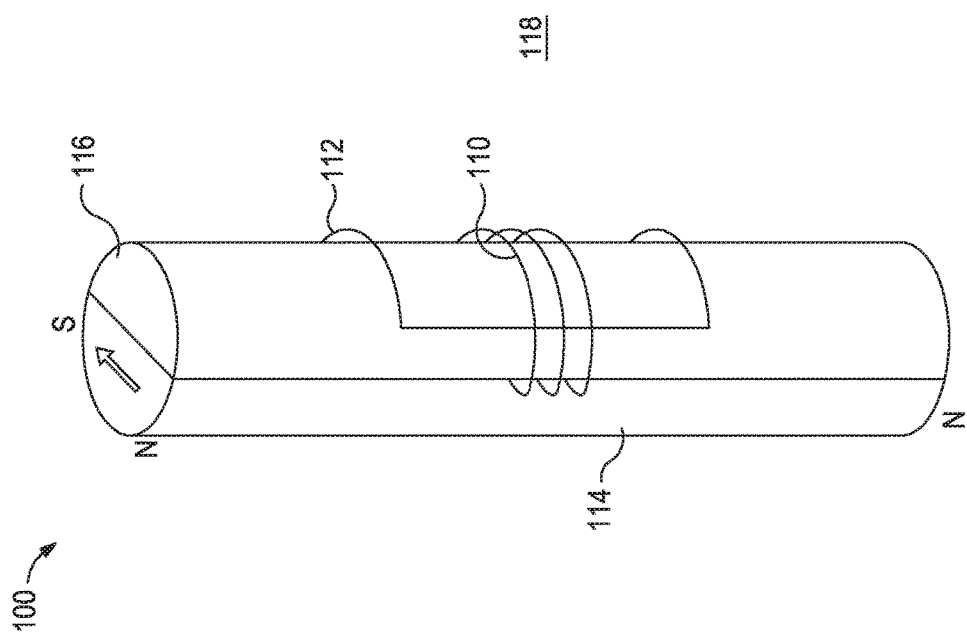

FIG. 1 illustrates an exemplary quadrature coil configuration 100 suitable for use in a side-looking NMR logging tool and including a z-coil 110, a transversal coil 112, a magnet 114, and a core material 116. In the illustrated quadrature coil configuration 100, the magnet 114 and the core material 116 are configured as two half cylinders that are associated to form a cylinder that would extend along at least a portion of the length of an associated NMR logging tool extendable within a wellbore. The two coils 110,112 are associated with the core material 116. In this configuration, relative to the axis of the of the cylinder formed by the magnet 114 and the core material 116, the z-coil 110 may be configured to generate a radiofrequency (RF) magnetic field (or excitation) $\vec{B}_{RF2}$ 120 in the axial direction, the transversal coil 112 may generate an RF magnetic field (or excitation) $\vec{B}_{RF1}$ 122 generally in the radial direction, and the magnet 114 and the core material 116 may cooperatively generate a static magnetic field $\vec{B}_0$ 124 generally in the tangential direction.

The three fields $\vec{B}_{RF2}$ 120, $\vec{B}_{RF1}$ 122, and $\vec{B}_0$ 124 have substantial components that are perpendicular to each other and satisfy a necessary condition for quadrature RF excitation and reception of an area of interest 118 being investigated by the NMR logging tool and located in front of the two coils 110,112. Further, in the illustrated quadrature coil configuration 100, the efficiency of the z-coil 110 ($|\vec{B}_{RF2}|/\sqrt{\text{power}}$, where power is the power used by the z-coil 110 to generate $\vec{B}_{RF2}$ 120) is almost always less than the efficiency of the transversal coil 112 ($|\vec{B}_{RF1}|/\sqrt{power}$, where power is the power used by the transversal coil 112 to generate $\vec{B}_{RF1}$) for the volumes of interest for NMR logging.

As used herein, the term "volume of interest" refers to the volume of the formation investigated by NMR. The thickness of the volume of interest is determined by $\vec{B}_{RF2}$ 120, $\vec{B}_{RF1}$ 122, and $\vec{B}_0$ 124 and, more specifically, the RF excitation pulse parameters (e.g., the bandwidth of the RF refocusing pulse in a Carr-Purcell-Meiboom-Gill (CPMG) echo train decay) and the magnetic field gradient of the logging instrument.

Generally, the RF excitation pulse parameters produced by one or both of the coils 110,112 interact with the protons in the surrounding environment (e.g., the area of interest 118) to produce an NMR signal that may then be received or detected by one or both of the coils 110,112, not necessarily the same coil 110,112 configuration used to produce the RF excitation pulse. The quadrature coil configuration 100 of the present disclosure allows for situation-dependent NMR logging operations to maximize the SNR and minimize the power consumption of the NMR logging tool. More specifically, depending on the wellbore diameter, composition of the fluid (e.g., fluid resistivity), depth of investigation, and the like, the quadrature coil configuration 100 of the present disclosure allows for choosing a transversal RF excitation or quadrature RF excitation (also known as circular RF excitation) in combination with either a transversal reception or quadrature reception. Transversal RF excitation may be achieved with the transversal coil 112, while quadrature RF excitation may be achieved with the z-coil 110 and transversal coil 112 being excited simultaneously. Then, transversal reception of the NMR signal may be achieved with the transversal coil 112, while quadrature reception may be achieved with the z-coil 110 and transversal coil 112 receiving at the same time.

While FIG. 1 illustrates $\vec{B}_0$ 124 generally in the tangential direction and $\vec{B}_{RF1}$ 122 in the radial direction. One can easily switch directions so that $\vec{B}_0$ 124 generally in the radial direction and $\vec{B}_{RF1}$ 122 in the tangential direction. Additionally, one may also design an NMR logging tool to be centralized instead of side-looking without departing from the principles of the present disclosure.

Regarding the fluid resistivity (also referred to herein as "mud resistivity") influence on the situational-dependent NMR logging operations disclosed herein, the fluid used in NMR logging operations may be either a water-based mud (WBM) (e.g., a brine), which is electrically conductive (i.e., has a low resistivity), or an oil-based mud (OBM), which is typically not electrically conductive (i.e., has a high resistivity). In an electrically conductive environment, the z-coil 110 will readily produce eddy currents closing around the NMR logging tool, which requires additional power to produce a suitable $\vec{B}_{RF2}$ 120. By contrast, in a nonconductive environment, the eddy currents produced by the z-coil 110 are forced to close around the wellbore, which covers a longer path and requires less energy. As a result, the z-coil 110 may be turned on or off to provide for transversal RF excitation or quadrature RF excitation based on the mud resistivity.

By way of nonlimiting example, when the fluid is an electrically conductive mud (e.g., a WBM), transversal RF excitation may be preferred.

By way of another nonlimiting example, for a side-looking operation when the fluid is not electrically conductive or has low electrical conductivity (e.g., an OBM), the preferred RF excitation may depend on the power available to implement the RF excitation and the relative efficiency of the two coils 110,112 ($|\vec{B}_{RF2}|/\sqrt{power}$ versus $|\vec{B}_{RF1}|/\sqrt{power}$). These two parameters are dependent on the NMR logging tool. Generally, more efficient of the transversal RF excitation or the quadrature RF excitation is preferred. However, where power is limited (e.g., in a logging-while-drilling tool), the power may dictate that the less efficient RF excitation be implemented based on power consumption of the coils 110,112. Using this methodology for analyzing the two parameters, a threshold excitation frequency can be calculated, which is unique to the NMR logging tool and the method of implementation (e.g., wireline versus logging-while-drilling). The threshold excitation frequency provides a demarcation of when the transversal RF excitation or the quadrature RF excitation should be used. Below the threshold excitation frequency, the quadrature RF excitation is implemented, while at or above the threshold excitation frequency, the transversal RF excitation is implemented.

Alternatively or in addition to the threshold excitation frequency, a threshold mud resistivity may be calculated based on the power available to implement the RF excitation, the relative efficiency of the two coils 110,112, and the mud resistivity. A quadrature RF excitation may be used for muds having a resistivity at or greater than the threshold mud resistivity, while muds having a resistivity less than threshold mud resistivity may indicate use of the transversal RF excitation. Generally, WBM will have a resistivity less than the threshold mud resistivity, so transversal RF excitation may be preferred.

For a centralized NMR logging tool, the eddy currents produced in conjunction with muds having a low electrical conductivity (e.g., some OBM) may be negligible and allow for quadrature RF excitation.

Regarding the wellbore diameter influence on the situational-dependent NMR logging operations disclosed herein, for a side-looking operation, the choice of RF excitation may depend on a tolerance to a wellbore signal produced from the back of the tool (i.e., opposite the area of interest 118). A side-focusing transversal coil 112 generates very little field at the back of the tool (i.e., opposite the area of interest 118). However, use of the z-coil 110 as part of the circular excitation may save power. Therefore, the use of the z-coil 110 in conjunction with quadrature RF excitation may depend on the tool configuration and specification and, more specifically, the porosity unit tolerance of the tool. The amount of signal from the back of the tool that can be attributed to the z-coil 110, which is based on the diameter of the wellbore and the diameter of the NMR logging tool, can be calculated. Based on this calculation, a threshold excitation frequency can be calculated in which an RF excitation frequency below the threshold excitation frequency may utilize the z-coil 110 (i.e., be a quadrature RF excitation), while an RF excitation frequency at or above the threshold excitation frequency may be a transversal RF excitation.

Alternatively or in addition to the threshold excitation frequency, a threshold wellbore diameter may be calculated based on the tool configuration and specification. A quadrature RF excitation may be used for wellbores having a diameter less than the threshold wellbore diameter, while wellbore diameters at or greater than threshold wellbore diameter may indicate use of the transversal RF excitation.

In some instances, the tool may include an active spoiler (not shown) that dampens the RF field generated in the back of the tool from the z-coil. Therefore, the use of an active spoiler should be considered in the calculation of the threshold excitation frequency and the threshold wellbore diameter.

Regarding the influence of a depth into the subterranean formation of the volume of investigation on the situational-dependent NMR logging operations disclosed herein, as the depth of the volume of investigation increases, the frequency and, consequently, the power consumption increase. Therefore, the available power and power requirements to achieve depths for the volumes of investigation may be used to calculate a threshold depth for the volumes of investigation, a threshold power level, or both. Frequencies and power consumption levels below their respective thresholds may allow for implementation of quadrature RF excitation, while frequencies and power consumption levels at or above their respective thresholds use transversal RF excitation.

A combination of any of the foregoing thresholds may be calculated and considered when determining which of the transversal RF excitation or quadrature RF excitations should be utilized in an NMR logging operation. For example, where multiple thresholds are calculated, when one of the thresholds indicates that transversal RF excitation is needed, the NMR logging tool may be set or configured for transversal RF excitation.

It is generally preferable to use quadrature coils for reception since reception using quadrature coils boosts SNR as compared to transversal coil only reception. However, the z-coil is more sensitive to signal from the wellbore in a side-looking logging situation and, consequently, may receive more NMR signal from the wellbore and fluids contained therein (referred to herein as "wellbore signal"). When the NMR signal combined from transversal coil and z-coil is greater than maximum wellbore signal (e.g., a predetermined threshold value based on the specifications of the NMR tool, the wellbore diameter, and the frequency of the RF excitation (i.e., the depth of the volume of interest)), the z-coil reception may be disabled, or the signal from z-coil may be discarded.

The quadrature coil configuration 100 described herein may allow a corresponding NMR logging tool to change excitation and reception modes independently while disposed in a wellbore. For example, in a WBM environment, when the wellbore diameter changes, the excitation mode may be changed. That is, when the wellbore becomes sufficiently small to negate or sufficiently mitigate NMR signals corresponding to the wellbore behind the tool, the NMR logging tool may be changed from transversal RF excitation to quadrature RF excitation, or vice versa when the wellbore diameter increases.

In addition to situational-dependent NMR logging operations, the NMR logging tools described herein with the two coils 110,112 that produce orthogonal fields $\vec{B}_{RF2}$ 120 and $\vec{B}_{RF1}$ 122, respectively, may be used for analyzing the resistivity of the subterranean formation. More particularly, when transmitting RF excitation pulses from the two coils 110,112, eddy currents are generated in the material surrounding the tool (i.e., the fluid and the formation). The eddy currents produced in the material surrounding the tool are similar in direction to the current flow through the two coils 110,112, which are orthogonal. Because OBMs have little to no resistivity, the eddy currents are predominantly from the formation. Therefore, measurement of the eddy currents in each of the orthogonal directions and a comparison thereof may be used to derive the formation anisotropy.

Generally, the quality factor (Q) of an NMR coil is the ratio of the peak magnetic energy stored by the coil divided by the average energy dissipated per radian by the coil. Equivalently, it can be expressed as the ratio of the reactive impedance ($\omega_0 L$) divided by the resistive impedance (R), which corresponds to the following equation: $Q=\omega_0 L/R$. As will be appreciated, the NMR coil coupling with the conductive surroundings affects the quality factor of the coils. Therefore, the quality factor for each of the two coils 110,112 may be measured and used to assess the formation resistivity. For example, the quality factor of the two coils 110,112 may be determined, in some instances, by applying a known RF excitation from each coil 110,112 and measuring the NMR signal from the subterranean formation. Then, the quality factor for each of the coils 110,112 may be calculated and compared (e.g., a ratio of the quality factors) to determine the formation anisotropy.

Figure 2:
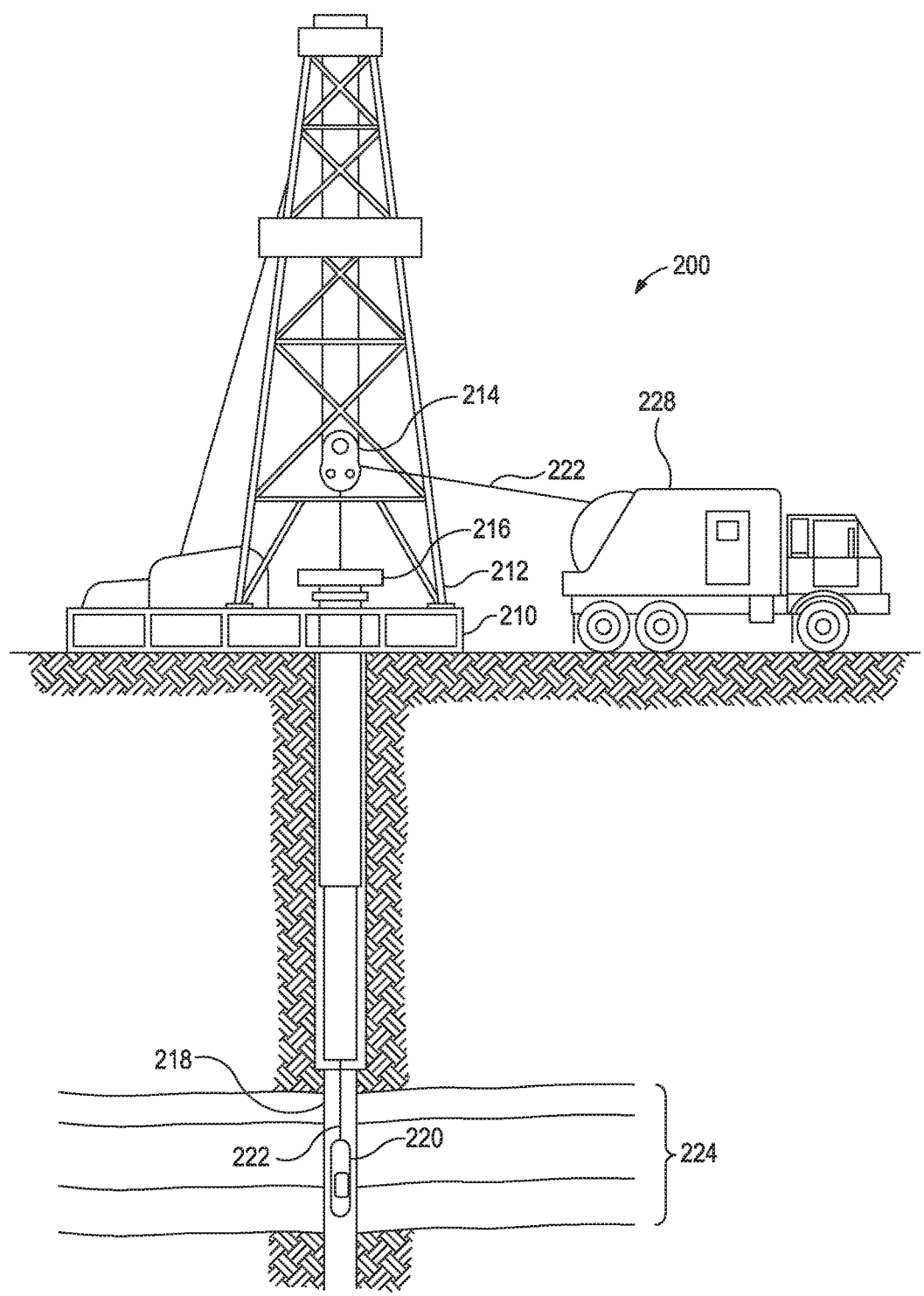
FIG. 2 is a wireline system suitable for performing NMR operations according to various embodiments described herein.

FIG. 2 is a wireline system 200 suitable for performing NMR operations according to various embodiments described herein. As illustrated, a drilling platform 210 may be equipped with a derrick 212 that supports a hoist 214. Drilling oil and gas wells is commonly carried out using a string of drill pipes connected together so as to form a drilling string that is lowered through a rotary table 216 into a wellbore 218. Here, it is assumed that the drilling string has been temporarily removed from the wellbore 218 to allow an NMR logging tool 220 to be lowered by wireline or logging cable 222 into the wellbore 218 containing the fluid (e.g., an OBM or a WBM).

Methods of the present disclosure may include introducing an NMR logging tool 220 with a z-coil and a transversal coil in to the wellbore 218 penetrating the subterranean formation 224. Typically, the NMR logging tool 220 is lowered to a region of interest and subsequently pulled upward at a substantially constant speed. During the upward trip, instruments included in the NMR logging tool 220 perform measurements in volumes of interest the subterranean formation 224 adjacent the wellbore 218 as the NMR logging tool 220 passes by.

For example, in some embodiments, either the transversal RF excitation (which is in a transversal direction relative to a z-axis that extends along the length of the wellbore) or the quadrature RF excitation may be generated as described herein in the volume of interest based on the resistivity of the fluid, a diameter of the wellbore 218, a depth into the subterranean formation 224 of the volume of investigation, or a combination thereof The NMR logging tool 220 may, then, detect the NMR signal from the subterranean formation 224 produced as a result of the RF excitation with either the transversal coil or both the z-coil and the transversal coil.

In another example, the NMR logging tool 220 may generate a quadrature RF signal and a transversal RF signal. The NMR signals corresponding to each RF signal may, then, be detected with either the transversal coil or both the z-coil and the transversal coil. The quality factor (Q) may be calculated for each of the z-coil and the transversal coil based on the NMR signals. The Q for each coil may be used to calculate the anisotropy of the subterranean formation 224.

The NMR relaxation data from either method may be communicated to a logging facility 228 for storage, processing, and analysis. The logging facility 228 may be provided with electronic equipment for various types of signal processing.

In some instances, the NMR logging tool 220 may be adapted for connection to a drill pipe for performing logging-while-drilling using the gradient multi-frequency NMR procedures described herein.

Embodiments disclosed herein include Embodiment A, Embodiment B, and Embodiment C.

Embodiment A is a method that includes introducing a NMR logging tool into a wellbore penetrating a subterranean formation, the wellbore containing a fluid and having a z-axis extending along a length of the wellbore, wherein the NMR logging tool has a z-coil and a transversal coil; generating in a volume of investigation of the subterranean formation either (1) a transversal RF excitation in a transversal direction relative to the z-axis of the wellbore with the transversal coil or (2) a quadrature RF excitation with both the z-coil and the transversal coil, wherein a selection between the transversal RF excitation and the quadrature RF excitation is based on a resistivity of the fluid, a diameter of the wellbore, a depth into the subterranean formation of the volume of investigation, or a combination thereof; and detecting an NMR signal from the subterranean formation produced as a result of the transversal RF excitation or the quadrature RF excitation with one of: (1) the transversal coil or (2) both the z-coil and the transversal coil.

Embodiment A may have one or more of the following additional elements in any combination: Element A1: wherein the fluid is an electrically conductive fluid and the method involves generating the transversal RF excitation; Element A2: wherein the NMR logging tool is configured for a side-looking operation and the fluid is an oil-based mud, wherein the method further involves: calculating a threshold excitation frequency based on a power availability for the NMR logging tool, an efficiency of the transversal coil, and an efficiency of the z-coil, and either (1) generating the transversal RF excitation with a frequency at or greater than the threshold excitation frequency or (2) generating the quadrature RF excitation at a frequency less than the threshold excitation frequency; Element A3: wherein the NMR logging tool is configured for a side-looking operation, the fluid is a mud, and the method further involves: calculating a threshold mud resistivity based on a power availability for the NMR logging tool, an efficiency of the transversal coil, and an efficiency of the z-coil, and either (1) generating the transversal RF excitation a resistivity of the mud is less than the threshold mud resistivity or (2) generating the quadrature RF excitation when the resistivity of the muds is at or greater than the threshold mud resistivity; Element A4: wherein the tool is configured for a centralized operation, the fluid is an oil-based mud, and the method involves generating the quadrature RF excitation; Element A5: wherein the NMR logging tool is configured for a side-looking operation and the fluid is an oil-based mud, wherein the method further involves: calculating a threshold excitation frequency based on a porosity unit tolerance of the NMR logging tool and a wellbore diameter, and either (1) generating the transversal RF excitation with a frequency at or greater than the threshold excitation frequency or (2) generating the quadrature RF excitation at a frequency less than the threshold excitation frequency; Element A6: wherein the NMR logging tool is configured for a side-looking operation and the fluid is an oil-based mud, wherein the method further involves: calculating a threshold wellbore diameter based on a porosity unit tolerance of the NMR logging tool, and either (1) generating the transversal RF excitation when a diameter of the wellbore is at or greater than the threshold wellbore diameter or (2) generating the quadrature RF excitation when the diameter of the wellbore is less than the threshold wellbore diameter; Element A7: wherein the NMR logging tool is configured for a side-looking operation and the fluid is an oil-based mud, wherein the method further involves: (A) at least two of (1) calculating a threshold excitation frequency based on a power availability for the NMR logging tool, an efficiency of the transversal coil, and an efficiency of the z-coil, (2) calculating a threshold mud resistivity based on the power availability for the NMR logging tool, the efficiency of the transversal coil, and the efficiency of the z-coil, (3) calculating a threshold excitation frequency based on a porosity unit tolerance of the NMR logging tool and a wellbore diameter, or (4) calculating a threshold wellbore diameter based on the porosity unit tolerance of the NMR logging tool; and (B) either: generating the quadrature RF excitation or generating the transversal RF excitation (1) with a frequency at or greater than the threshold excitation frequency, (2) when a resistivity of the mud is less than the threshold mud resistivity, or (4) when a diameter of the wellbore is at or greater than the threshold wellbore diameter; Element A8: wherein detecting an NMR signal from the subterranean formation is with the transversal coil; and Element A9: wherein detecting an NMR signal from the subterranean formation is with the both the z-coil and the transversal coil.

By way of non-limiting example, exemplary combinations applicable to Embodiment A include: Element A1 in combination with Element A8 or Element A9; Element A2 in combination with Element A8 or Element A9; Element A3 in combination with Element A8 or Element A9; Element A4 in combination with Element A8 or Element A9; Element A5 in combination with Element A8 or Element A9; Element A6 in combination with Element A8 or Element A9; and Element A7 in combination with Element A8 or Element A9.

Embodiment B is a method that includes introducing a NMR logging tool into a wellbore penetrating a subterranean formation, the wellbore containing a fluid and having a z-axis extending along a length of the wellbore, wherein the NMR logging tool has a z-coil and a transversal coil; generating a plurality of RF excitations each corresponding to different volumes of interest in the subterranean formation, wherein the plurality of RF excitations includes a transversal RF excitation in a transversal direction relative to the z-axis of the wellbore with the transversal coil and a quadrature RF excitation with the z-coil and the transversal coil, wherein a frequency corresponding to the quadrature RF excitation is less than a frequency corresponding to the transversal RF excitation; and detecting an NMR signal from the subterranean formation produced as a result of the transversal RF excitation or the quadrature RF excitation with one of: (1) the transversal coil or (2) both the z-coil and the transversal coil.

Embodiment B may have one or more of the following additional elements in any combination: Element B1: wherein the NMR logging tool is configured for a side-looking operation and the fluid is an oil-based mud; wherein the method further involves: calculating a threshold excitation frequency based on a power availability for the NMR logging tool, an efficiency of the transversal coil, and an efficiency of the z-coil; and wherein a frequency of the transversal RF excitation is at or greater than the threshold excitation frequency and a frequency of the quadrature RF excitation is less than the threshold excitation frequency; Element B2: wherein the NMR logging tool is configured for a side-looking operation and the fluid is an oil-based mud; wherein the method further involves: calculating a threshold excitation frequency based on a porosity unit tolerance of the NMR logging tool and a wellbore diameter;

and wherein a frequency of the transversal RF excitation is at or greater than the threshold excitation frequency and a frequency of the quadrature RF excitation is less than the threshold excitation frequency; Element B3: wherein detecting an NMR signal from the subterranean formation is with the transversal coil; and Element B4: wherein detecting an NMR signal from the subterranean formation is with the both the z-coil and the transversal coil.

By way of non-limiting example, exemplary combinations applicable to Embodiment B include: Element B1 in combination with Element B3 or Element B4; and Element B2 in combination with Element B3 or Element B4.

Embodiment C is a method that includes introducing a nuclear magnetic resonance (NMR) logging tool in a wellbore penetrating a subterranean formation, the wellbore containing an oil-based mud (OBM) and having a z-axis extending along a length of the wellbore, wherein the NMR logging tool having a transversal dipole magnet, a z-coil, and a transversal coil; generating a quadrature radiofrequency (RF) excitation with the z-coil and the transversal coil; generating a transversal RF excitation in a transversal direction relative to the z-axis of the wellbore with the transversal coil; detecting a first NMR signal and second NMR signal from the formation produced by the quadrature RF excitation and the transversal RF excitation, respectively, with one of: (1) the transversal coil or (2) both the z-coil and the transversal coil; calculating a quality factor for each of the z-coil and the transversal coil based on the first and second NMR signals relative to the quadrature RF excitation and the transversal RF excitation, respectively; and calculating a formation anisotropy based on the quality factor for the z-coil and the quality factor for the transversal coil.

Embodiment C may have one the following additional elements: Element C1: wherein detecting an NMR signal from the subterranean formation is with the transversal coil; and Element C2: wherein detecting an NMR signal from the subterranean formation is with the both the z-coil and the transversal coil.

Embodiment D is a system that includes a wellbore penetrating a subterranean formation containing a fluid and having a z-axis extending along a length of the wellbore; and a nuclear magnetic resonance (NMR) logging tool extendable within the wellbore and having a z-coil and a transversal coil, wherein the NMR logging tool generates in a volume of investigation of the subterranean formation either (1) a transversal radiofrequency (RF) excitation in a transversal direction relative to the z-axis of the wellbore with the transversal coil or (2) a quadrature RF excitation with both the z-coil and the transversal coil, a selection between the transversal RF excitation and the quadrature RF excitation being based on a resistivity of the fluid, a diameter of the wellbore, a depth into the subterranean formation of the volume of investigation, or a combination thereof, and wherein the NMR logging tool detects an NMR signal from the subterranean formation produced as a result of the transversal RF excitation or the quadrature RF excitation with one of the transversal coil or both the z-coil and the transversal coil.

Embodiment D may have one the following additional elements: Element D1: wherein the NMR logging tool is configured for a side-looking operation and the fluid is an oil-based mud, wherein a threshold excitation frequency is calculated based on a power availability for the NMR logging tool, an efficiency of the transversal coil, and an efficiency of the z-coil, and wherein either (1) the transversal RF excitation is generated with a frequency at or greater than the threshold excitation frequency or (2) the quadrature RF excitation is generated at a frequency less than the threshold excitation frequency; Element D2: wherein the NMR logging tool is configured for a side-looking operation and the fluid is a drilling fluid, wherein a threshold mud resistivity is calculated based on a power availability for the NMR logging tool, an efficiency of the transversal coil, and an efficiency of the z-coil, and wherein either (1) the transversal RF excitation is generated when a resistivity of the mud is less than the threshold mud resistivity or (2) the quadrature RF excitation is generated when the resistivity of the muds is at or greater than the threshold mud resistivity; Element D3: wherein the NMR tool operates while centralized within the wellbore and generates the quadrature RF excitation; Element D4: wherein the NMR logging tool is configured for a side-looking operation and the fluid is an oil-based mud, wherein a threshold excitation frequency is calculated based on a porosity unit tolerance of the NMR logging tool and a wellbore diameter, and wherein either (1) the transversal RF excitation is generated with a frequency at or greater than the threshold excitation frequency or (2) the quadrature RF excitation is generated at a frequency less than the threshold excitation frequency; Element D5: wherein the NMR logging tool is configured for a side-looking operation and the fluid is an oil-based mud, wherein a threshold wellbore diameter is calculated based on a porosity unit tolerance of the NMR logging tool, and wherein either (1) the transversal RF excitation is generated when a diameter of the wellbore is at or greater than the threshold wellbore diameter or (2) the quadrature RF excitation is generated when the diameter of the wellbore is less than the threshold wellbore diameter; and, Element D6: wherein the NMR signal from the subterranean formation is detected by at least one coil selected from the group consisting of the z-coil, the transversal coil, and the combination thereof.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Simulations were performed using a quadrature coil configuration of FIG. 1 with a 8.5" diameter bore hole to investigate the SNR produced and power used for various depths of investigation (DOI). Tables 1 and 2 provide the results of the simulations using OBM and WBM, respectively.

TABLE 1

OBM

|  |  | 1.5" DOI | 2.0" DOI | 3.0" DOI | 4.0" DOI |
|---|---|---|---|---|---|
| transversal RF excitation and reception | SNR | 27 | 21 | 16 | 13 |
|  | power (kw) | 0.11 | 0.17 | 0.35 | 0.63 |
| quadrature RF excitation and reception | SNR | 35 | 30 | 25 | 22 |
|  | power (kw) | 0.28 | 0.36 | 0.54 | 0.77 |

TABLE 2

WBM

|  |  | 1.5" DOI | 2.0" DOI | 3.0" DOI | 4.0" DOI |
|---|---|---|---|---|---|
| transversal RF excitation and reception | SNR | 19 | 16 | 13 | 11 |
|  | power (kw) | 0.23 | 0.34 | 0.60 | 0.98 |
| quadrature RF excitation and reception | SNR | 23 | 19 | 17 | 15 |
|  | power (kw) | 1.93 | 2.41 | 3.27 | 4.25 |

In an OBM environment (Table 1), quadrature RF excitation and reception substantially increases the SNR gain for all DOIs with minimal increases in power consumption. In a WBM environment (Table 2), the quadrature RF excitation and reception does enhance the SNR but with greater power requirements, which may exceed the limits of the electronics.

In additional simulations under the same wellbore conditions, transversal RF excitation was simulated with transversal or quadrature reception.

TABLE 3

SNR with transversal RF excitation

|  |  | 1.5" DOI | 2.0" DOI | 3.0" DOI | 4.0" DOI |
|---|---|---|---|---|---|
| OBM | transversal RF reception | 27 | 21 | 16 | 13 |
|  | quadrature RF reception | 29 | 23 | 19 | 16 |
| WBM | transversal RF reception | 19 | 16 | 13 | 11 |
|  | quadrature RF reception | 20 | 16 | 14 | 12 |

The SNR improves by using quadrature reception for both mud compositions. As the DOI goes deeper, the SNR improvement becomes more substantial because of the relative efficiency gain of the z-coil.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
   introducing a nuclear magnetic resonance (NMR) logging tool into a wellbore penetrating a subterranean formation, the wellbore containing a fluid and having a z-axis extending along a length of the wellbore, wherein the NMR logging tool has a z-coil and a transversal coil;
   generating in a volume of investigation of the subterranean formation either (1) a transversal radiofrequency (RF) excitation in a transversal direction relative to the z-axis of the wellbore with the transversal coil or (2) a quadrature RF excitation with both the z-coil and the transversal coil, wherein a selection between the transversal RF excitation and the quadrature RF excitation is based on a resistivity of the fluid, a diameter of the wellbore, a depth into the subterranean formation of the volume of investigation, or a combination thereof; and
   detecting an NMR signal from the subterranean formation produced as a result of the transversal RF excitation or the quadrature RF excitation with one of: (1) the transversal coil or (2) both the z-coil and the transversal coil.

2. The method of claim 1, wherein the fluid is an electrically conductive fluid and the method involves generating the transversal RF excitation.

3. The method of claim 1, wherein the NMR logging tool is configured for a side-looking operation and the fluid is an oil-based mud, wherein the method further involves: calculating a threshold excitation frequency based on a power availability for the NMR logging tool, an efficiency of the transversal coil, and an efficiency of the z-coil, and either (1) generating the transversal RF excitation with a frequency at or greater than the threshold excitation frequency or (2) generating the quadrature RF excitation at a frequency less than the threshold excitation frequency.

4. The method of claim 1, wherein the NMR logging tool is configured for a side-looking operation, the fluid is a mud and the method further involves: calculating a threshold mud resistivity based on a power availability for the NMR logging tool, an efficiency of the transversal coil, and an efficiency of the z-coil, and either (1) generating the transversal RF excitation when a resistivity of the mud is less than the threshold mud resistivity or (2) generating the quadrature RF excitation when the resistivity of the muds is at or greater than the threshold mud resistivity.

5. The method of claim 1, wherein the tool is configured for a centralized operation, the fluid is an oil-based mud, and the method involves generating the quadrature RF excitation.

6. The method of claim 1, wherein the NMR logging tool is configured for a side-looking operation and the fluid is an oil-based mud, wherein the method further involves: calculating a threshold excitation frequency based on a porosity unit tolerance of the NMR logging tool and a wellbore diameter, and either (1) generating the transversal RF excitation with a frequency at or greater than the threshold excitation frequency or (2) generating the quadrature RF excitation at a frequency less than the threshold excitation frequency.

7. The method of claim 1, wherein the NMR logging tool is configured for a side-looking operation and the fluid is an oil-based mud, wherein the method further involves: calculating a threshold wellbore diameter based on a porosity unit tolerance of the NMR logging tool, and either (1) generating the transversal RF excitation when a diameter of the wellbore is at or greater than the threshold wellbore diameter or (2) generating the quadrature RF excitation when the diameter of the wellbore is less than the threshold wellbore diameter.

8. The method of claim 1, wherein detecting an NMR signal from the subterranean formation is with the transversal coil.

9. The method of claim 1, wherein detecting an NMR signal from the subterranean formation is with both the z-coil and the transversal coil.

10. A method comprising:
introducing a nuclear magnetic resonance (NMR) logging tool into a wellbore penetrating a subterranean formation, the wellbore containing a fluid and having a z-axis extending along a length of the wellbore, wherein the NMR logging tool has a z-coil and a transversal coil;
generating a plurality of radiofrequency (RF) excitations each corresponding to different volumes of interest in the subterranean formation, wherein the plurality of RF excitations includes a transversal RF excitation in a transversal direction relative to the z-axis of the wellbore with the transversal coil and a quadrature RF excitation with the z-coil and the transversal coil, wherein a frequency corresponding to the quadrature RF excitation is less than a frequency corresponding to the transversal RF excitation; and
detecting an NMR signal from the subterranean formation produced as a result of the transversal RF excitation or the quadrature RF excitation with one of: (1) the transversal coil or (2) both the z-coil and the transversal coil.

11. The method of claim 10, wherein the NMR logging tool is configured for a side-looking operation and the fluid is an oil-based mud; wherein the method further involves: calculating a threshold excitation frequency based on a power availability for the NMR logging tool, an efficiency of the transversal coil, and an efficiency of the z-coil; and wherein a frequency of the transversal RF excitation is at or greater than the threshold excitation frequency and a frequency of the quadrature RF excitation is less than the threshold excitation frequency.

12. The method of claim 10, wherein the NMR logging tool is configured for a side-looking operation and the fluid is an oil-based mud; wherein the method further involves: calculating a threshold excitation frequency based on a porosity unit tolerance of the NMR logging tool and a wellbore diameter; and wherein a frequency of the transversal RF excitation is at or greater than the threshold excitation frequency and a frequency of the quadrature RF excitation is less than the threshold excitation frequency.

13. The method of claim 10, wherein detecting the NMR signal from the subterranean formation is with the transversal coil.

14. The method of claim 10, wherein detecting the NMR signal from the subterranean formation is with both the z-coil and the transversal coil.

15. A method comprising:
introducing a nuclear magnetic resonance (NMR) logging tool into a wellbore penetrating a subterranean formation, the wellbore containing an oil-based mud (OBM) and having a z-axis extending along a length of the wellbore, wherein the NMR logging tool having a transversal dipole magnet, a z-coil, and a transversal coil;
generating a quadrature radiofrequency (RF) excitation with the z-coil and the transversal coil;
generating a transversal RF excitation in a transversal direction relative to the z-axis of the wellbore with the transversal coil;
detecting a first NMR signal and a second NMR signal from the subterranean formation produced by the quadrature RF excitation and the transversal RF excitation, respectively, with one of: (1) the transversal coil or (2) both the z-coil and the transversal coil;
calculating a quality factor for each of the z-coil and the transversal coil based on the first and second NMR signals relative to the quadrature RF excitation and the transversal RF excitation, respectively; and
calculating a formation anisotropy based on the quality factor for the z-coil and the quality factor for the transversal coil.

16. The method of claim 15, wherein detecting the first NMR signal and the second NMR signal from the subterranean formation is with the transversal coil.

17. The method of claim 15, wherein detecting the first NMR signal and the second NMR signal from the subterranean formation is with both the z-coil and the transversal coil.

18. A system comprising:
a wellbore penetrating a subterranean formation containing a fluid and having a z-axis extending along a length of the wellbore; and
a nuclear magnetic resonance (NMR) logging tool extendable within the wellbore and having a z-coil and a transversal coil,
wherein the NMR logging tool generates in a volume of investigation of the subterranean formation either (1) a transversal radiofrequency (RF) excitation in a transversal direction relative to the z-axis of the wellbore with the transversal coil or (2) a quadrature RF excitation with both the z-coil and the transversal coil, a selection between the transversal RF excitation and the quadrature RF excitation being based on a resistivity of the fluid, a diameter of the wellbore, a depth into the subterranean formation of the volume of investigation, or a combination thereof, and wherein the NMR logging tool detects an NMR signal from the subterranean formation produced as a result of the transversal RF excitation or the quadrature RF excitation with one of the transversal coil or both the z-coil and the transversal coil.

19. The system of claim 18, wherein the NMR logging tool is configured for a side-looking operation and the fluid is an oil-based mud, wherein a threshold excitation frequency is calculated based on a power availability for the NMR logging tool, an efficiency of the transversal coil, and an efficiency of the z-coil, and wherein either (1) the transversal RF excitation is generated with a frequency at or greater than the threshold excitation frequency or (2) the quadrature RF excitation is generated at a frequency less than the threshold excitation frequency.

20. The system of claim 18, wherein the NMR logging tool is configured for a side-looking operation and the fluid is a drilling fluid, wherein a threshold mud resistivity is calculated based on a power availability for the NMR logging tool, an efficiency of the transversal coil, and an efficiency of the z-coil, and wherein either (1) the transversal RF excitation is generated when a resistivity of the mud is less than the threshold mud resistivity or (2) the quadrature RF excitation is generated when the resistivity of the muds is at or greater than the threshold mud resistivity.

21. The system of claim 18, wherein the NMR tool operates while centralized within the wellbore and generates the quadrature RF excitation.

22. The system of claim 18, wherein the NMR logging tool is configured for a side-looking operation and the fluid is an oil-based mud, wherein a threshold excitation frequency is calculated based on a porosity unit tolerance of the NMR logging tool and a wellbore diameter, and wherein either (1) the transversal RF excitation is generated with a frequency at or greater than the threshold excitation frequency or (2) the quadrature RF excitation is generated at a frequency less than the threshold excitation frequency.

23. The system of claim 18, wherein the NMR logging tool is configured for a side-looking operation and the fluid is an oil-based mud, wherein a threshold wellbore diameter is calculated based on a porosity unit tolerance of the NMR logging tool, and wherein either (1) the transversal RF excitation is generated when a diameter of the wellbore is at or greater than the threshold wellbore diameter or (2) the quadrature RF excitation is generated when the diameter of the wellbore is less than the threshold wellbore diameter.

24. The system of claim 18, wherein the NMR signal from the subterranean formation is detected by at least one coil selected from the group consisting of the z-coil, the transversal coil, and the combination thereof.

* * * * *